(12) United States Patent
Ben-Shalom et al.

(10) Patent No.: US 7,695,255 B2
(45) Date of Patent: Apr. 13, 2010

(54) PERISTALTIC PUMP

(75) Inventors: Zvi Ben-Shalom, Yavne (IL); Ori Goldor, Givat Ada (IL); Roni Shabat, Kibbutz (IL); Shaul Ozeri, Tel-Aviv (IL)

(73) Assignee: Q-Core Medical Ltd, Petach Tikva (IL)

( * ) Notice: Subject to any disclaimer, the term of this patent is extended or adjusted under 35 U.S.C. 154(b) by 909 days.

(21) Appl. No.: 10/535,103

(22) PCT Filed: Nov. 12, 2003
(Under 37 CFR 1.47)

(86) PCT No.: PCT/IL03/00947
§ 371 (c)(1),
(2), (4) Date: May 16, 2005

(87) PCT Pub. No.: WO2004/044424
PCT Pub. Date: May 27, 2004

(65) Prior Publication Data
US 2008/0095649 A1    Apr. 24, 2008

(30) Foreign Application Priority Data
Nov. 14, 2002    (IL) .................................... 152865

(51) Int. Cl.
*F04B 43/09* (2006.01)
*H02K 7/065* (2006.01)

(52) U.S. Cl. .................. 417/412; 417/474; 417/479; 310/23; 310/36

(58) Field of Classification Search ................ 417/412, 417/474, 479; 310/23, 24, 15, 21, 36
See application file for complete search history.

(56) References Cited

U.S. PATENT DOCUMENTS

| 2,056,322 A | 10/1936 | Hoppe |
| 2,743,898 A | 5/1956 | King |

(Continued)

FOREIGN PATENT DOCUMENTS

DE    101 18 086 A1    7/2002

(Continued)

OTHER PUBLICATIONS

International Application PCT/IL1997/000290 Search Report dated Jan. 27, 1998.

(Continued)

*Primary Examiner*—Charles G Freay
(74) *Attorney, Agent, or Firm*—D. Kligler I.P. Services Ltd

(57) ABSTRACT

A pump for generating fluid flow in an elastic tubular conduit. The pump comprises a plurality of electrically operated valves, each valve being positionable adjacent to the conduit. Each valve has a valve head configured to alternate from a first position in which the lumen of the conduit adjacent to the valve head is unobstructed and a second position in which the lumen of the conduit adjacent to the valve head is obstructed. The pump also comprises a driver configured to control the positions of the valve heads, so as to execute a predetermined temporo-spatial array of valve head positions.

2 Claims, 18 Drawing Sheets

U.S. PATENT DOCUMENTS

| | | |
|---|---|---|
| 3,443,585 A | 5/1969 | Reinicke |
| 3,982,722 A | 9/1976 | Bernard |
| 3,982,725 A | 9/1976 | Clark |
| 4,014,318 A * | 3/1977 | Dockum et al. ............... 600/16 |
| 4,039,269 A | 8/1977 | Pickering |
| 4,155,362 A * | 5/1979 | Jess ........................... 604/507 |
| 4,236,880 A | 12/1980 | Archibald et al. |
| 4,270,532 A * | 6/1981 | Franetzki et al. ............ 604/151 |
| 4,320,781 A | 3/1982 | Bouvet et al. |
| 4,450,375 A | 5/1984 | Siegal |
| 4,489,863 A | 12/1984 | Horchos et al. |
| 4,682,135 A | 7/1987 | Yamakawa |
| 4,741,736 A * | 5/1988 | Brown ......................... 604/134 |
| 4,893,991 A | 1/1990 | Heminway et al. |
| 4,978,335 A | 12/1990 | Arthur, III |
| 5,152,680 A | 10/1992 | Okada |
| 5,213,483 A | 5/1993 | Flaherty et al. |
| 5,257,978 A | 11/1993 | Haber et al. |
| 5,290,158 A | 3/1994 | Okada |
| 5,395,320 A | 3/1995 | Padda et al. |
| 5,509,439 A | 4/1996 | Tantardini |
| 5,527,295 A | 6/1996 | Wing |
| 5,575,309 A | 11/1996 | Connell |
| 5,577,891 A * | 11/1996 | Loughnane et al. ........... 417/53 |
| 5,593,134 A | 1/1997 | Steber et al. |
| 5,658,252 A | 8/1997 | Johnson |
| 5,683,233 A | 11/1997 | Moubayed et al. |
| 5,782,805 A | 7/1998 | Meinzer et al. |
| 5,807,322 A | 9/1998 | Lindsey et al. |
| 5,896,076 A | 4/1999 | Van Namen |
| 5,996,964 A | 12/1999 | Ben-Shalom |
| 6,095,189 A | 8/2000 | Ben-Shalom |
| 6,203,296 B1 | 3/2001 | Ray et al. |
| 6,261,262 B1 | 7/2001 | Briggs et al. |
| 6,339,410 B1 | 1/2002 | Milner et al. |
| 6,371,732 B1 | 4/2002 | Moubayed et al. |
| 6,450,773 B1 * | 9/2002 | Upton ......................... 417/53 |
| 6,537,244 B2 | 3/2003 | Paukovits et al. |
| 6,692,241 B2 | 2/2004 | Watanabe et al. |
| 6,733,476 B2 | 5/2004 | Christenson et al. |
| 7,018,361 B2 * | 3/2006 | Gillespie et al. ............ 604/151 |
| 7,022,075 B2 | 4/2006 | Grunwald et al. |
| 2002/0156402 A1 | 10/2002 | Woog et al. |
| 2002/0165503 A1 | 11/2002 | Morris et al. |
| 2003/0040700 A1 | 2/2003 | Hickle et al. |
| 2003/0182586 A1 | 9/2003 | Numano |
| 2004/0181314 A1 | 9/2004 | Zaleski |
| 2005/0088409 A1 | 4/2005 | Van Berkel |
| 2006/0051218 A1 | 3/2006 | Harttig |
| 2007/0269324 A1 | 11/2007 | Goldor et al. |

FOREIGN PATENT DOCUMENTS

| | | |
|---|---|---|
| FR | 2632529 A | 12/1989 |
| JP | 60 043188 | 3/1985 |
| JP | 2004141418 A | 5/2004 |
| WO | 03/027503 A1 | 4/2003 |

OTHER PUBLICATIONS

International Application PCT/IL2007/001398 Search Report dated Jun. 11, 2008.
International Application PCT/IL2007/001398 Patentability Report dated May 28, 2009.
International Application PCT/IL2007/001399 Search Report dated Jun. 4, 2008.
International Application PCT/IL2007/001399 Patentability Report dated May 19, 2009.
International Application PCT/IL2007/001400 Search Report dated Jul. 15, 2008.
International Application PCT/IL2007/001400 Patentability Report dated May 28, 2009.
International Application PCT/IL2007/001401 Search Report dated Sep. 24, 2008.
International Application PCT/IL2007/001401 Patentability Report dated May 28, 2009.
International Application PCT/IL2007/001402 Search Report dated Jun. 20, 2008.
International Application PCT/IL2007/001402 Patentability Report dated May 28, 2009.
International Application PCT/IL2007/001404 Search Report dated Jul. 14, 2008.
International Application PCT/IL2007/001404 Patentability Report dated May 28, 2009.
International Application PCT/IL2007/001405 Search Report dated Jul. 21, 2008.
International Application PCT/IL2007/001405 Patentability Report dated May 28, 2009.
International Application PCT/IL2005/001249 Search Report dated Apr. 5, 2006.
U.S. Appl. No. 09/125,438 Official dated May 3, 1999.
Chinese Patent Application No. 200580045471.3 "Finger-type peristaltic pump" Official Action dated Jul. 18, 2008.
U.S. Appl. No. 09/125,438 Official dated Jul. 15, 1999.
International Application PCT/IL1997/000289 Search report dated Jan. 27, 1998.
European Application No. 05810500.8 Official Action dated Jul. 6, 2009.

* cited by examiner

|  $a_1$ | $a_2$ | $a_3$ | $a_4$ |
|---|---|---|---|
| 1 | 1 | 0 | 0 |

~500

505 ⇩

| 0 | 1 | 1 | 0 | ~510 |

515 ⇩

| 0 | 0 | 1 | 1 | ~520 |

525 ⇩

| 1 | 0 | 0 | 1 | ~530 |

535 ⇩

| 1 | 1 | 0 | 0 | ~500 |

FIG. 4

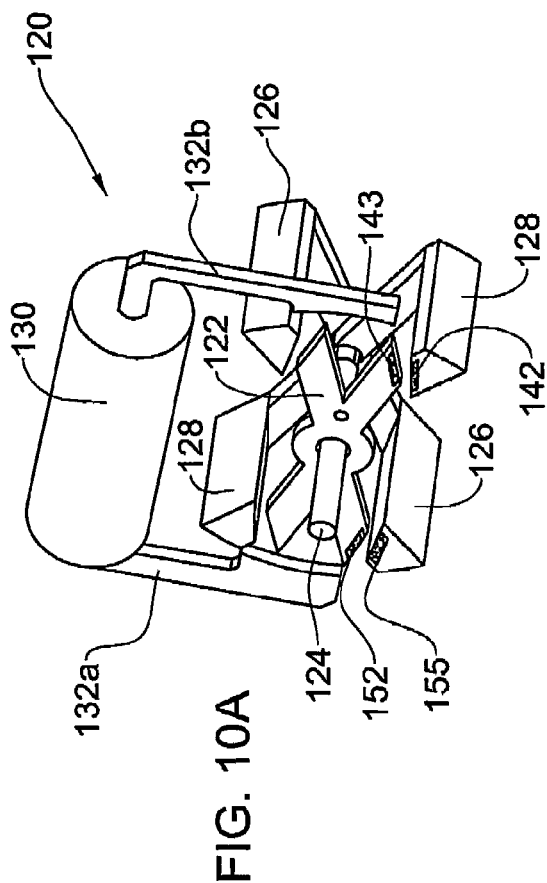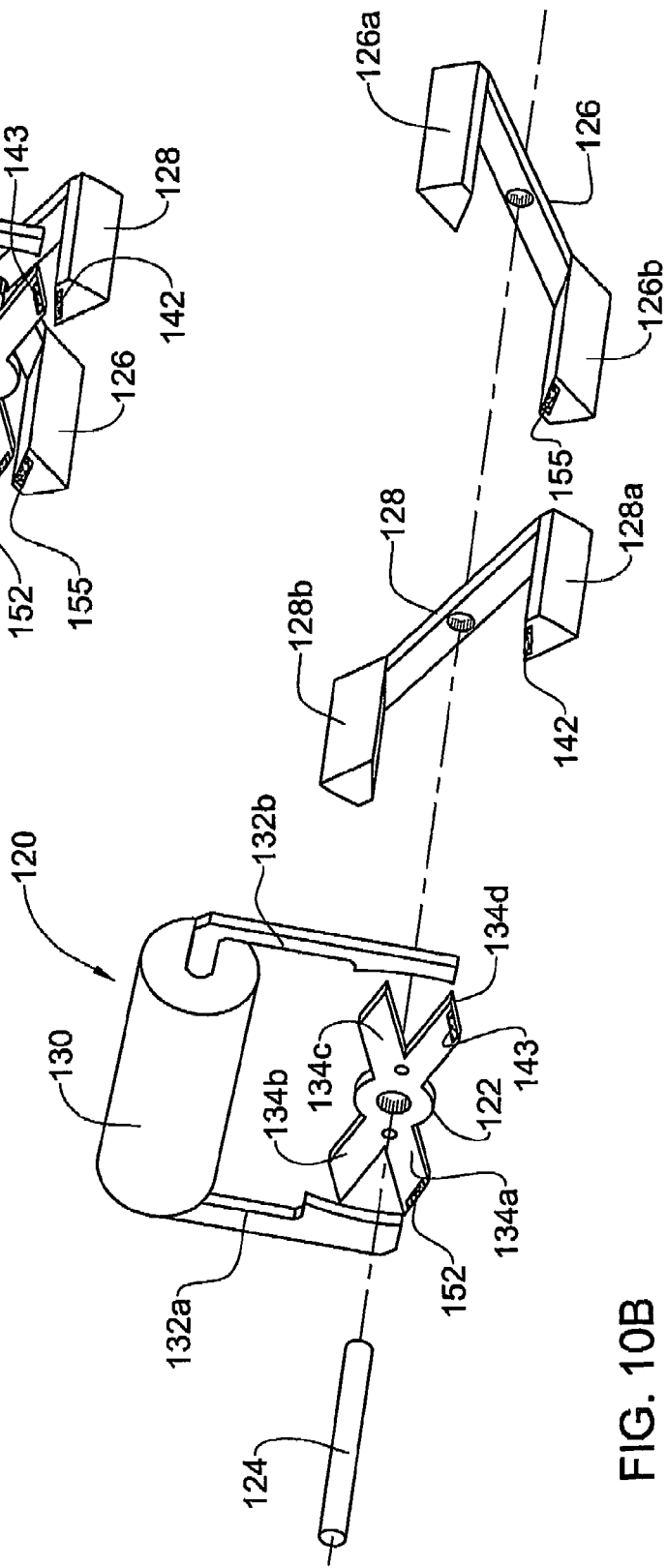

PERISTALTIC PUMP

FIELD OF THE INVENTION

This invention relates to devices for controlling fluid flow.

BACKGROUND OF THE INVENTION

Peristaltic pumps are used for controlling the flow of a fluid in an elastic tubular conduit. These pumps have many medical and industrial applications.

In one form of peristaltic pumps, a rotor is used to rotate a plurality of eccentric cams. Each cam, in turn, intermittently collapses the elastic conduit at an initial contact point, and slides along the conduit over a short distance as the rotor turns. A second cam contacts the initial contact point and the first cam is then released from the conduit as the second cam slides along the conduit. As this process is repeated, a flow of fluid in the conduit is generated in the direction of the sliding of the cams.

U.S. Pat. No. 5,996,964 to Ben-Shalom discloses a peristaltic pump in which a plurality of electromagnets are arranged along an elastic conduit. The electromagnets are activated according to a temporo-spatial scheme in order to generate undulations along a magnetizable membrane that is disposed along the conduit. The undulations in the membrane generate undulations in the wall of the conduit, which in turn generate a flow of fluid in the conduit.

SUMMARY OF THE INVENTION

The present invention provides a peristaltic pump for generating a flow of fluid in a elastic tubular conduit. The pump comprises a plurality of electrically operated valves that are arranged along the conduit. Each valve has a valve head that alternates between two positions, referred to herein as the "up position" and a "down position". The designations "up", "down", "left" and "right" are used herein only for the sake of clarity in describing the invention, and the invention is not limited to any particular orientation. When a valve head is in its down position, the valve head presses on a segment of the conduit so as to obstruct the lumen of the conduit in the segment, thus preventing fluid from entering the segment. When the valve head is in its up position, the lumen of the conduit in the segment is open, and fluid may flow into the segment.

Electric power from a power supply is distributed among the valves according to a predetermined temporo-spatial pattern by a driver unit. This generates a temporo-spatial array of valve head positions, which in turn generates a flow of fluid in the conduit.

The invention thus provides a pump for generating fluid flow in an elastic tubular conduit having a lumen, comprising:
(a) a plurality of electrically operated valves, each valve being positionable adjacent to the conduit, each valve having a valve head, the valve head configured to alternate from a first position in which the lumen of the conduit adjacent to the valve head is unobstructed and a second position in which the lumen of the conduit adjacent to the valve head is obstructed;
(b) a driver configured to control the positions of the valve heads, so as to execute a predetermined temporo-spatial array of valve head positions.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 4 shows a temporo-spatial array of valve activation for a pump having 4 valves in accordance with another embodiment of the invention;

FIG. 10a shows a perspective view and FIG. 10b shows an exploded view of a driving mechanism for use in a peristaltic pump of the invention;

DETAILED DESCRIPTION OF THE INVENTION

Figure 1:
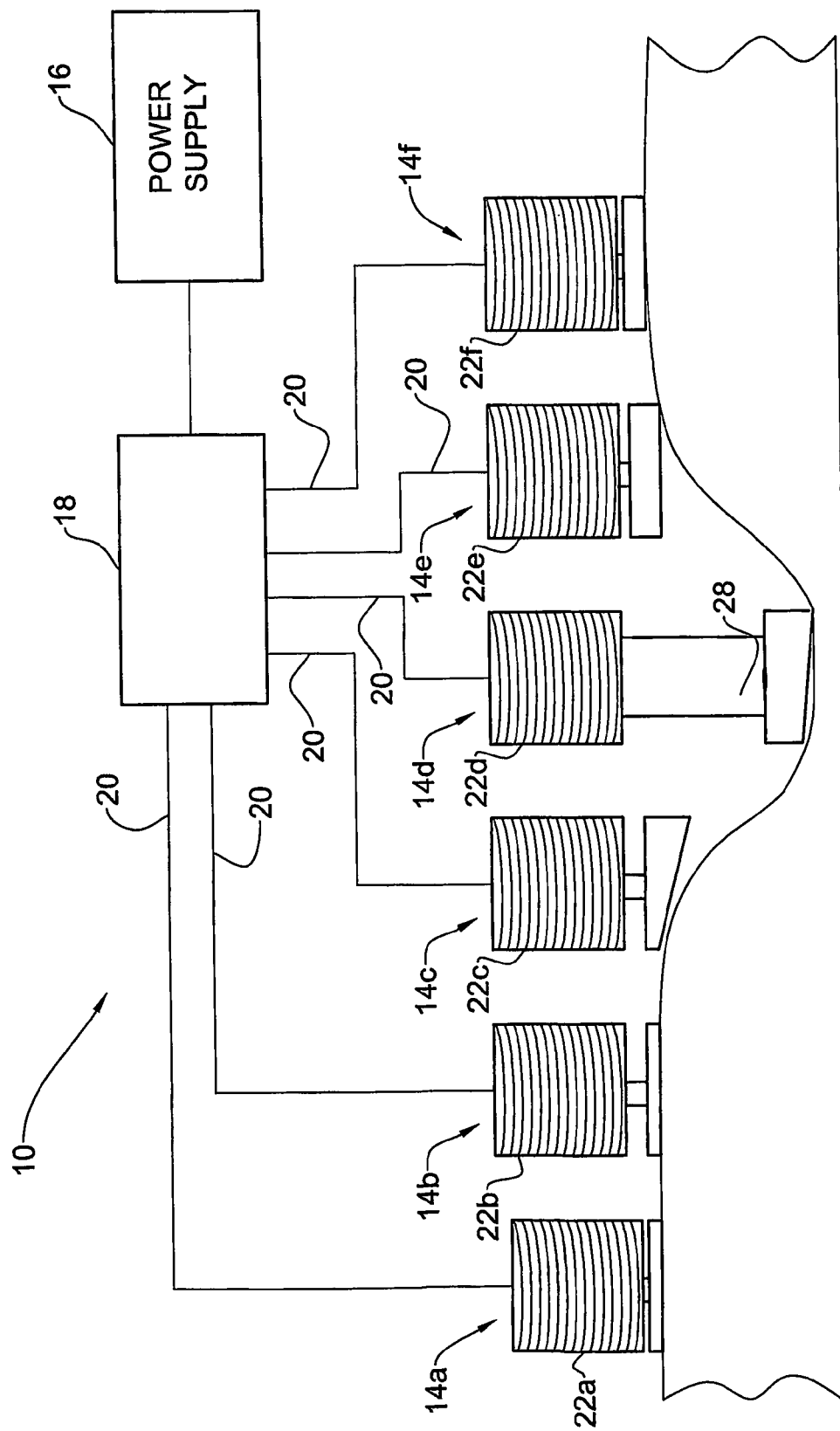
FIG. 1 shows a peristaltic pump in accordance with one embodiment of the invention.

FIG. 1 shows schematically a peristaltic pump generally referred to as 10 in accordance with one embodiment of the invention. The pump 10 is used to generate a flow of fluid in a tubular conduit 12 having an elastic wall. The tubular conduit 12 may have any cross-sectional shape such as circular, square, rectangular, and so on. A plurality of electrically operated valves 14 are arranged along the conduit 12. Electric power from a power supply 16 is distributed among the valves according to a predetermined temporo-spatial pattern by a driver unit 18 via cables 20.

Figure 2A:
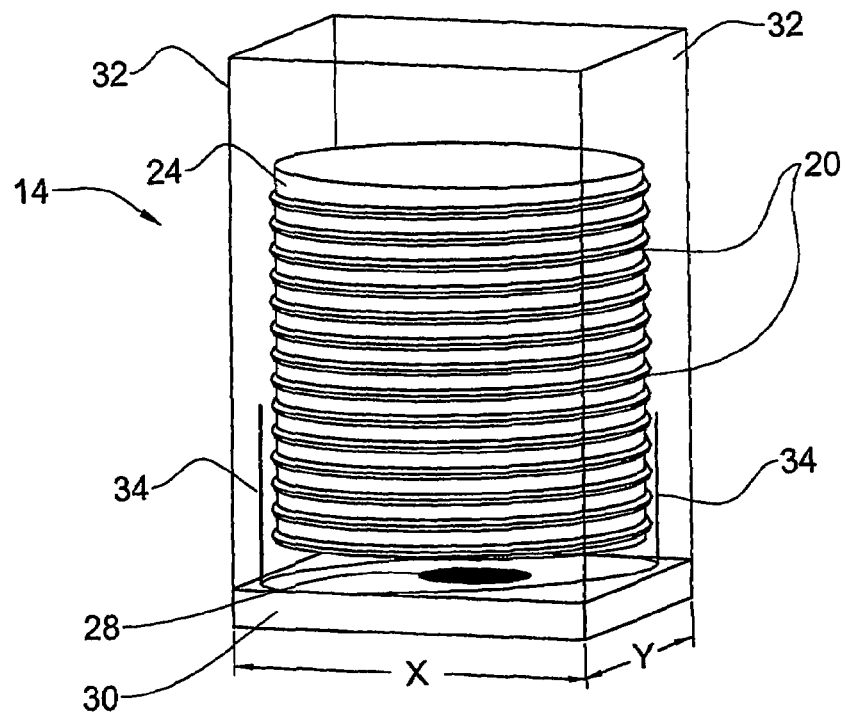
FIG. 2 shows a valve used in the pump of FIG. 1.
Figure 2B:
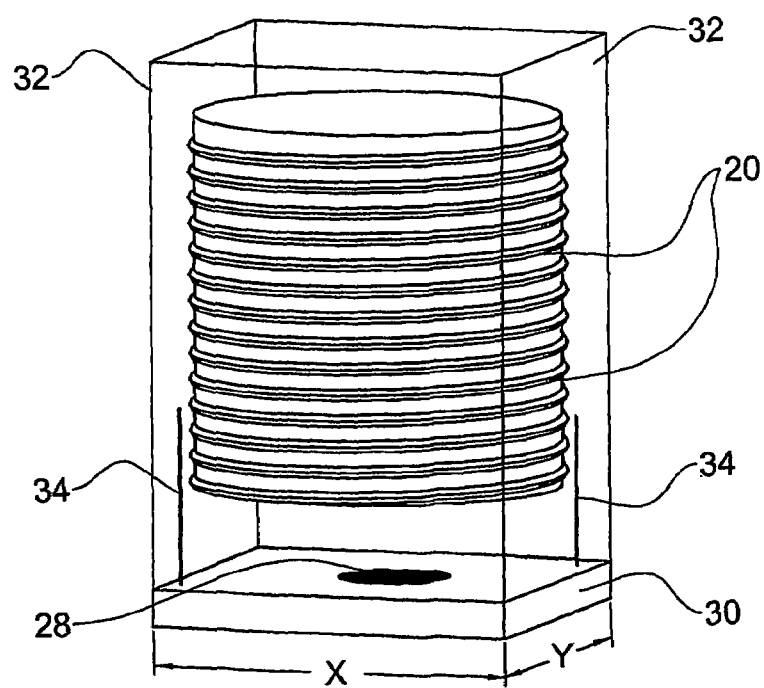

FIG. 2 shows the structure of the valve 14 in detail. The valve 14 comprises an electromagnet formed from a wire coil 24. A permanent magnet 28 is attached to a valve head 30. When current flows in a first direction in the coil 24, a magnetic field is generated that raises the magnet 28 and head 30 so as to position them proximate to the electromagnet 24 as shown in FIG. 2a. When current flows in the opposite direction in the coil 24, a magnetic field is generated that lowers the magnet 28 and head 30 so as to position them distal to the electromagnet 24, as shown in FIG. 2b. The coil 24 is enclosed in a cylindrical housing 32. Guide rods 34 maintain the head 30 coaxial with electromagnet 24 as the head travels from the position shown in FIG. 2a (referred to herein as the "up position") to the position shown in FIG. 2b (referred to herein as the "down position").

As shown in FIG. 2, the head 30 may have a rectangular cross-section when viewed along the longitudinal axis of the coil 24. This is by way of example only, and the head 30 may have any shape as required in any particular application. For a head having a rectangular cross section, one dimension of the rectangular cross-section (indicated by y in FIG. 2) is selected to be slightly larger than half the circumference of the conduit 12 (i.e. slightly larger than the width of the conduit when flattened).

Referring again to FIG. 1, the valves 14 are oriented adjacent to the conduit 12 with the y dimension perpendicular to the axis of the conduit 12. The other dimension of the head 30 (indicated by x in FIGS. 1 and 2) is parallel to the axis of the conduit 12. As seen in FIG. 1, the x-dimension may be different for different valves. Thus, for example, the x-dimension of valve 14a is greater than the x-dimension of valve 14b. The head of the valve 14a, for example, is shown in its up position. The head of the valve 14d is shown in its down position.

When a valve head is in its down position, the lumen of the segment adjacent to the valve is obstructed, and fluid cannot flow into the segment. As shown in FIG. 1, the valve head preferable contacts the conduit 12 obliquely, for example by an angle θ of about 4°. Due to the elasticity of the conduit, when a valve head is brought from its down position to its up position, the lumen of the segment of the conduit adjacent to the valve becomes unobstructed, and fluid may flow into that segment of the conduit. The elastic conduit 12 is preferably pre-loaded by limiting the elastic expansion of a segment of the conduit when the valve head adjacent to the segment is brought from its down position to its up position, so that some elastic strain is always present in all segments of the conduit adjacent to valve heads. This decreases the variability in the volume flow that occurs when a valve moves from one position to another.

The driver 18 is configured to determine the polarity of a voltage applied to the coil 24 of each valve 14 according to a predetermined temporo-spatial array of voltages, so as to generate the temporo-spatial array of the positions (up or down) of the valve heads 30 that generates a flow of fluid in the conduit 12.

Figure 3:
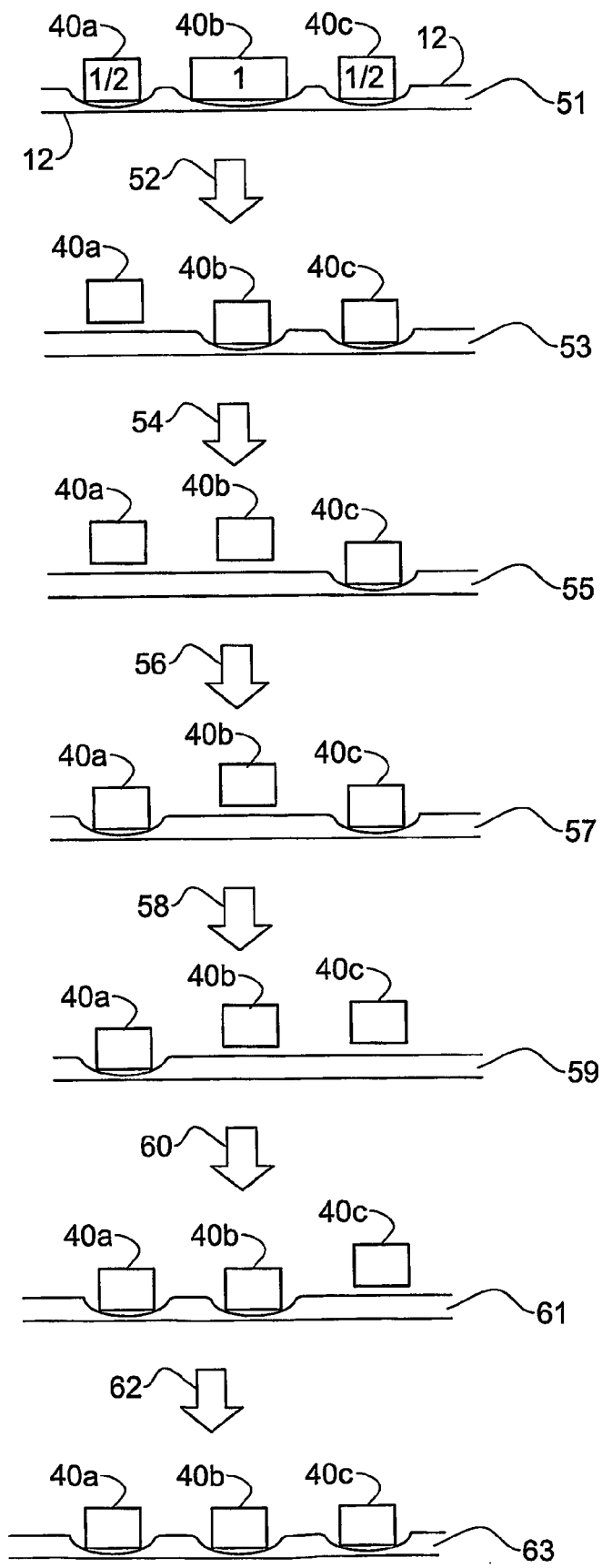
FIG. 3 shows a temporo-spatial array of valve activation for a pump having three valves in accordance with one embodiment of the invention.

FIG. 3 shows schematically an example of a temporo-spatial array of valve activation that may be used with the pump of the invention. This is by way of example, and any temporo-spatial array of valve positions that generates a flow of fluid in the conduit 12 may be used with the pump of the invention. The example of FIG. 3 relates to a pump having three valves. This, however, is only to simplify the explanation of the operation of the pump, and, a pump in accordance with the invention may have any number of valves. For simplicity, only the valve heads 40a, 40b and 40c of the valves is shown in FIG. 3.

In the initial configuration 51 of the valve heads, the three valve heads 40a, 40b and 40c are in their down position so that the lumen of the conduit 12 is obstructed in the segments of the conduit 12 adjacent to the valve heads 40a, 40b, and 40c. In stroke 52, the valve head 40a is brought to its up position, so that the lumen of the conduit 12 is open under the valve 40a. The pump now has the configuration 53. Stroke 52 causes fluid to flow into the conduit 12 in the portion of the lumen that was opened by raising valve 40a from its down position to its up position. The flow of fluid is from left to right under the valve head 40a. The volume of fluid that flows is proportional to the x-dimension of the head of the valve 40a. In stroke 54, valve head 40b is raised to its up position, so that the pump acquires the configuration 55. Stroke 54 causes fluid to flow into the segment of conduit 12 that was opened by raising valve 40b from its down position to its up position. No fluid flows out of the pump during stroke 54. In stroke 56, valve head 40a is lowered. Stroke 56 causes an amount of fluid that is proportional to the x-dimension of the valve head 40a to flow from left to right under the valve head 40b. The pump now has the configuration 57. In stroke 58, valve head 40c is raised to its up position, so that the pump assumes the configuration 59. Stroke 58 causes an amount of fluid proportional to the x-dimension of the valve head 40c to flow in the negative direction under the valve head 40c.

In stroke 60, valve head 40b is lowered causing an amount of fluid proportional to the x-dimension of the valve head 40b to flow in the positive direction. The pump thus acquires the configuration 61. In stroke 62, the valve 40c is lowered, causing 1 volume unit to flow in the positive direction. The valve heads 40 are now all in their down position, and the cyclic temporo-array may begin again.

FIG. 4 shows a temporo-spatial array for activating a pump having 4 valves. For convenience, a valve head in its down position is represented as a 1, and a valve in the up position is represented as a 0. The four valve heads are referred to as $a_1$, $a_2$, $a_3$, and $a_4$. This array begins with valve heads $a_1$ and $a_2$ in their down position, and valve heads $a_3$ and $a_4$ in their up position (configuration 500). In the first stroke of the pump (stroke 505), valve head $a_1$ is raised and valve $a_3$ is lowered, and the pump acquires the configuration 510. Valve head $a_2$ is then raised and valve $a_4$ is lowered (stroke 515) so that the pump acquires the configuration 520. Valve head $a_1$ is then lowered and valve head $a_3$ is raised (stroke 525) leading to configuration 530. Valve head $a_2$ is then lowered and valve head $a_4$ is raised (stroke 535). The configuration of the pump thus returns to configuration 500, and the cycle may begin again.

Figure 5A:
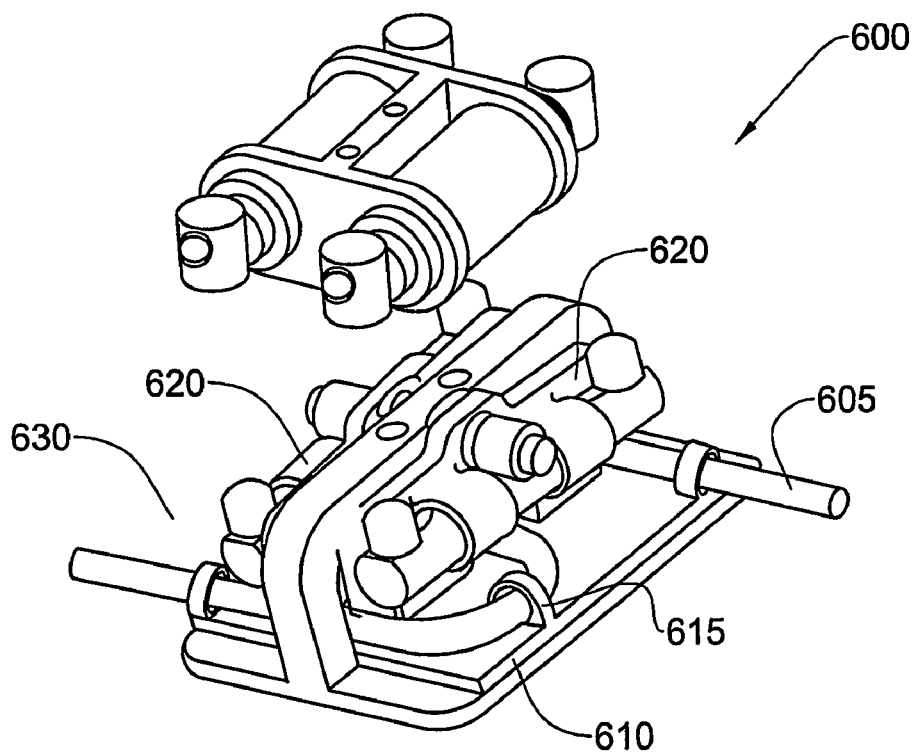
FIG. 5 shows a peristaltic pump having 4 valves arranged in two dual valves in accordance with another embodiment of the invention.
Figure 5B:
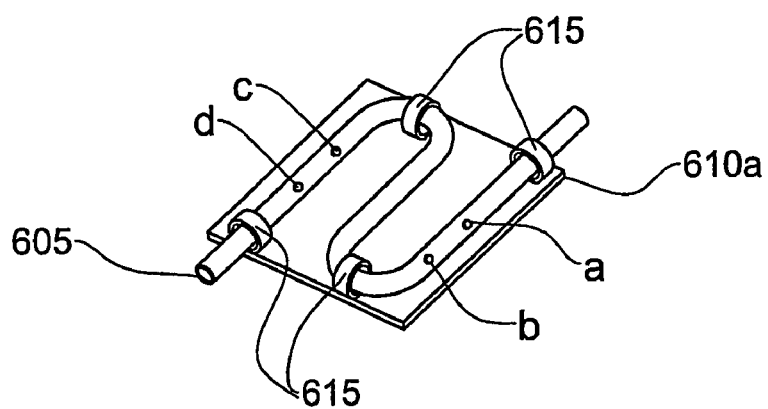

FIG. 5 shows a pump 600 in accordance with another embodiment of the invention that executes the temporo-spatial array of valve activation shown in FIG. 4. In this embodiment, a segment of a elastic tubular conduit 605 is fixed to a base 610 by clips 615 so that the segment of the conduit 605 fixed to the base 610 has an "S" shape, as shown in FIG. 5b.

Figure 6A:
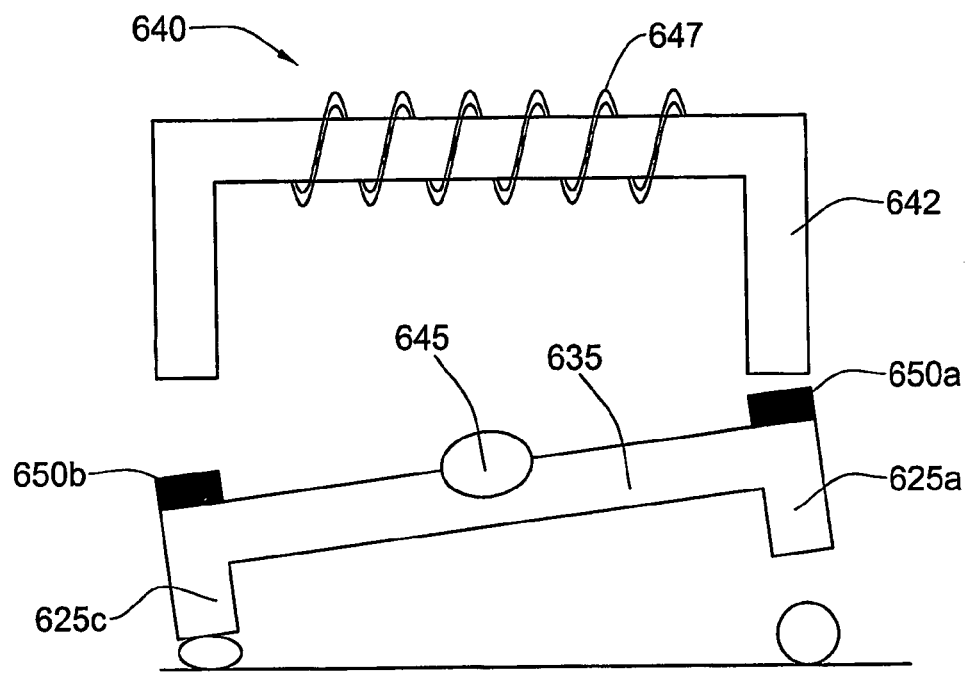
FIG. 6 shows the construction of a dual valve.
Figure 6B:
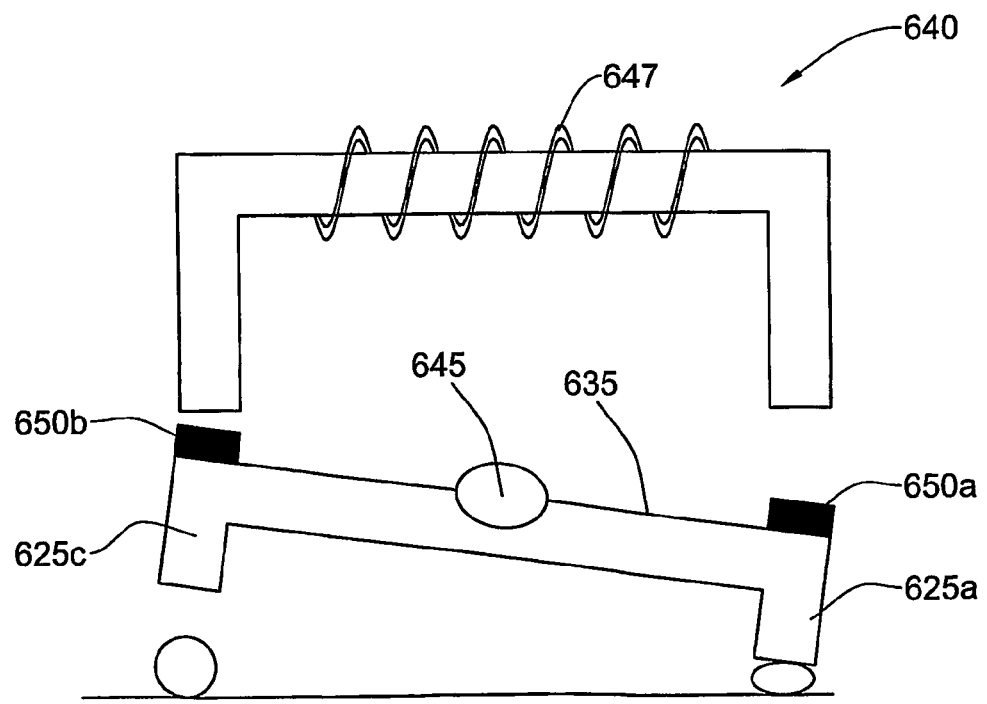

The pump 600 comprises two dual valves 620a and 620b. The dual valve 620a has two valve heads 625a and 625c, and the dual valve 620b has two valve heads 625b and 625d. The dual valves are fixed to the base 610 via a bracket 630 so that the valve heads 625a, 625b, 625c and 625d are located over the points a, b, c, and d, respectively, along the conduit 605. Each of the valve heads 625 has an up position in which the lumen in the conduit 605 under the valve head is open allowing fluid flow, and a down position in which the lumen under the valve head is obstructed, preventing fluid flow. The design of the dual valve 620a is shown schematically in FIG. 6. The valve heads 625a and 625c are attached to opposite ends of an iron bar 635. The lever bar is pivotable around an axle 645. When the lever bar is in the configuration shown in FIG. 6a, the valve head 625a is in its up configuration, and the valve head 625c is in its down configuration. When the lever bar is in the configuration shown in FIG. 6b, the valve head 625a is in its down configuration, and the valve head 625c is in its up configuration. Movement of the lever bar is controlled by an electromagnet 640. A "U" shaped iron bar 642 passes through the interior of a wire coil 647. A pair of permanent magnets 650a and 650b are attached at either end of the lever bar. When current flows in one direction in the coil 647, the lever bar assumes the configuration shown in FIG. 6a. Attraction between the magnet 650a and the bar 642 latches the lever bar in this configuration. When current flows in the other direction in the coil 647, the lever bar switches to the configuration shown in FIG. 6b. Attraction between the magnet 650b to the bar 642 latches the lever bar in this configuration. Operation of the dual valve 620b is similar to that just described for dual valve 620a.

Due to the construction of the dual valve 620a, the valve head 625a and 625c are never both open or closed simultaneously. Similarly, the valve heads 625b and 625d are never both opened or closed simultaneously. Note that in the temporo-spatial array of valve positions shown in FIG. 4 that is to be executed by embodiment, valve heads $a_1$ and $a_3$ are never open or closed simultaneously. This also applies to valves $a_2$ and $a_4$.

Figure 7:
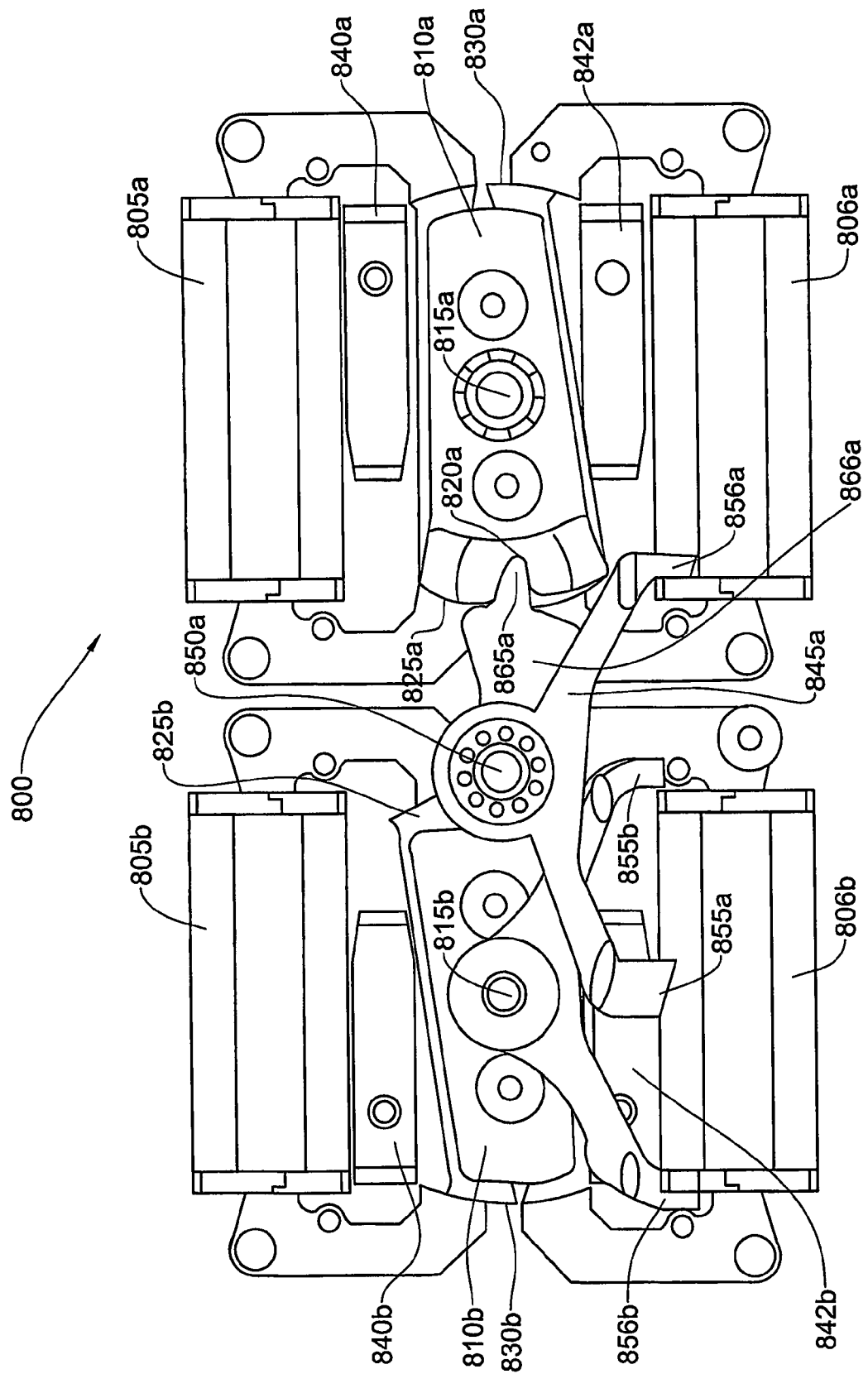
FIG. 7 shows a peristaltic pump in accordance with another embodiment of the invention.

FIG. 7 shows another embodiment of a pump in accordance with the invention that executes the temporo-spatial array of valve activation shown in FIG. 4. In this embodiment, a lever 810a is rotatable around a pivot 815a. The lever 810a has a notch 820a at a notched end 825a that is close to the center of the pump 800. The lever 810a is pivotable around the pivot 815a from a first position in which the notch 820a is lowered as shown in FIG. 7, and a second position in which the notch 820a is raised (not shown). The position of the lever 810a is determined by a pair of electromagnets 805a and 806a. When the electromagnet 805a is activated, the lever 810a assumes its first position in which the notch 820 is lowered. A permanent magnet 840a latches the lever 810a in this position. When the electromagnet 806a is activated, the lever 810a assumes its second position in which the notch 820 is raised. A permanent magnet 842a latches the lever 810 in this position.

A second lever 845a has a first valve head 855a and a second valve head 856a. The lever 845a is rotatable about a pivot 850a from a first position in which the valve head 855a is higher than the valve head 856a, as shown in FIG. 7, and a second position in which the valve head 855a is lower than the valve head 856a. The lever 845a includes an extension 860a having a terminal projection 865a that mates with the notch 820a. The position of the lever 845a is determined by the position of the lever 810a. When the lever 810a is in its first or second position, the lever 845a is also in its first or second position, respectively.

Another lever 810b is rotatable around a pivot 815b. The lever 810b is pivotable around the pivot 815b from a first position in which a first end 825b is raised, as shown in FIG. 7, and a second position in which the first end 825b is lowered (not shown). The position of the lever 810b is determined by a pair of electromagnets 805b and 806b. When the electromagnet 806b is activated, the lever 810b assumes its first position. A permanent magnet 842b latches the lever 810b in this position. When the electromagnet 805b is activated, the lever 810b assumes its second position. A permanent magnet 840b latches the lever 810b in this position.

A lever 845b has a first valve head 855b and a second valve head 856b. The lever 845b is rotatable about the pivot 815b from a first position in which the valve head 855b is higher than the valve head 856b, as shown in FIG. 7, and a second position in which the valve head 855b is lower than the valve head 856b. When the lever 810b is in its first or second position, the lever 845b is also in its first or second position, respectively.

The temporo-spatial array of activation of the four electromagnets 805a, 806a, 805b, and 806b, is determined by a driver (not shown) so as to activate a predetermined temporo-spatial array of valve head positions. Valve heads 855a, and 856a are never open or closed simultaneously. The same also applies to 855b and 856b. This is consistent with the temporo-spatial array of valve head activation shown in FIG. 4.

Figure 8:
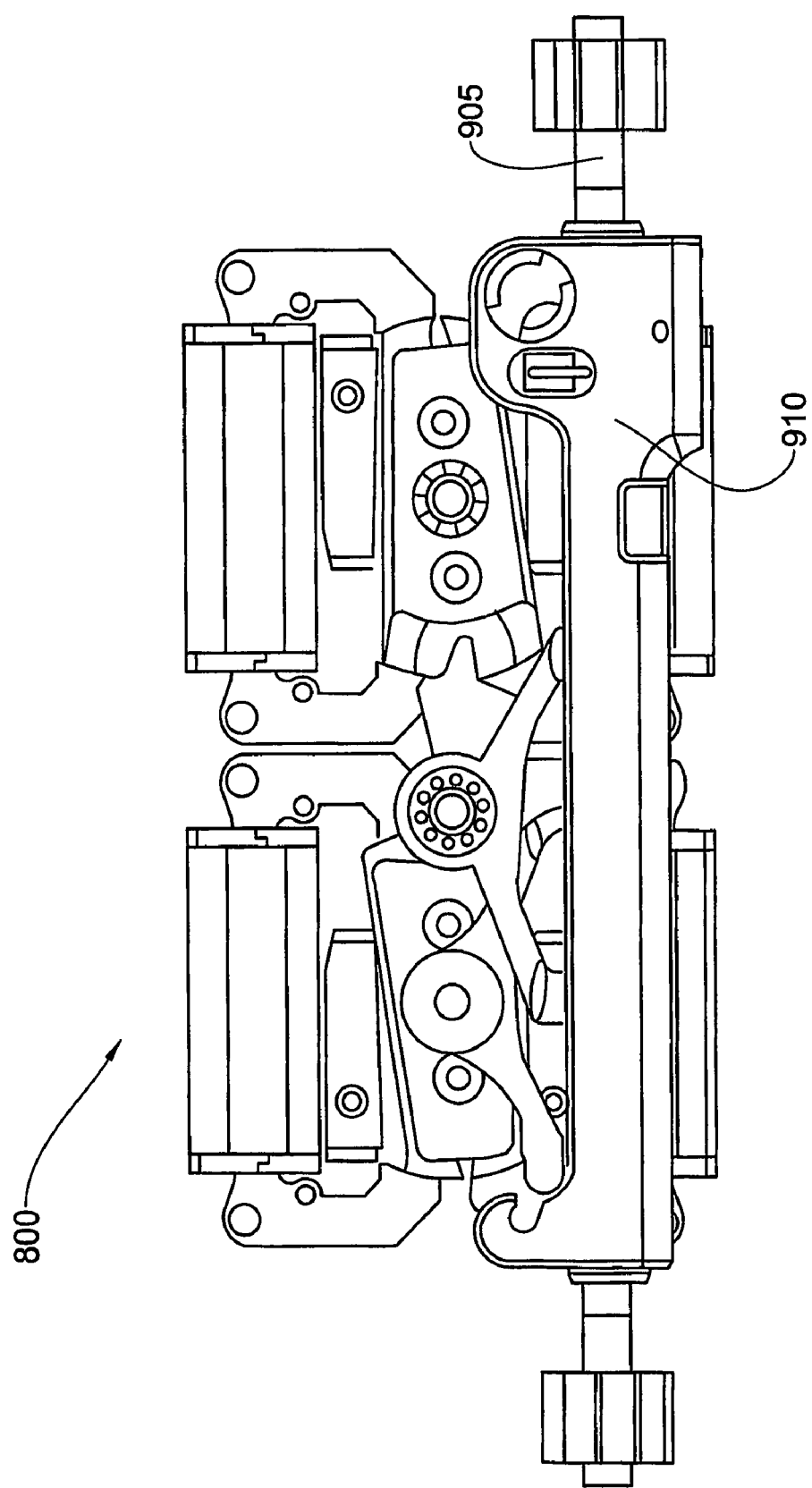
FIG. 8 shows the pump of FIG. 7 in conjunction with an elastic tubular conduit held in a sleeve.

FIG. 8 shows the pump 800 in conjunction with an elastic tubular conduit 905. The tubular conduit 905 is held in a sleeve 910. The sleeve 910 is reversibly attached onto the pump 800 so that when the lever 845a is in its first position, the segment of the tubular conduit 905 adjacent to the valve head 855a is unobstructed while the portion of the tubular conduit 905 adjacent to the valve head 856a is obstructed. The conduit 905 is adapted at each of its end to mate with extension conduits (not shown), for example, by means of male and female luer fittings at either end. The conduit 905 and the sheath may be provided as a single disposable unit.

Figure 9:
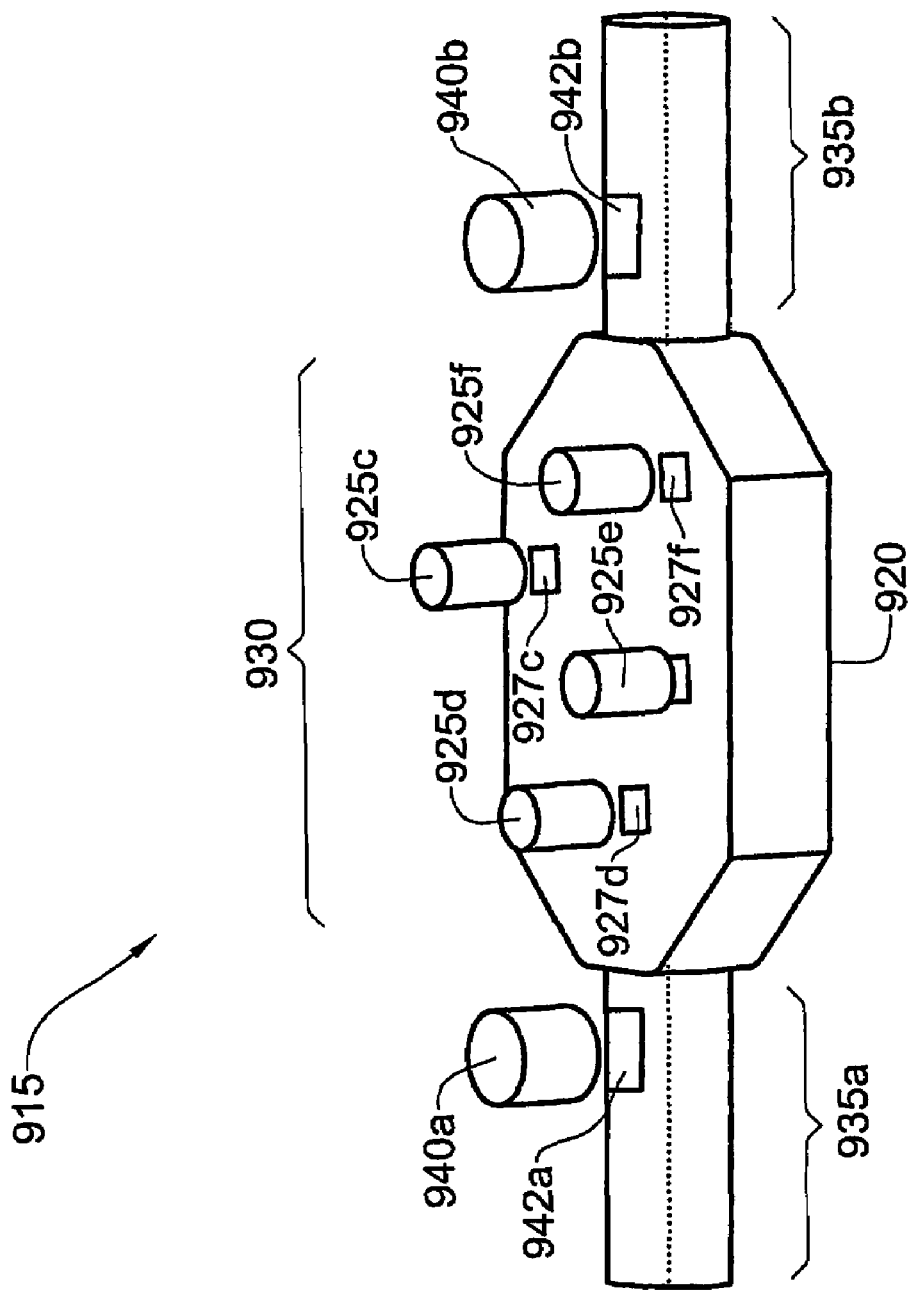
FIG. 9 shows a pump in accordance with another embodiment of the invention.

FIG. 9 shows schematically another embodiment of a pump in accordance with another embodiment of the invention. This embodiment, generally indicated by 915, is used for generating fluid flow in an elastic tubular conduit 920 having a section 930 of large cross sectional area (referred to herein as the "expanded section"), flanked by regions 935a and 935b of small cross section area (referred to herein as the "narrow sections").

The pump includes one or more valves 925 that are positionable adjacent to the expanded section 930 of the conduit 920. Valves 940a and 940b are postionable adjacent to the narrow section 935a and 935b, respectively. Four valves 925 are shown in FIG. 9. This is by example only, and any number of valves 925 maybe used as required by any particular application. The valves 925 and the valves 940 may have for example, the structure described above in reference to FIG. 2. Each of the valves 925 has a valve head 927, and each of the valves 940 has a valve head 942. The valve heads 927 have an up position in which a portion of the expanded section 930 adjacent to the valve is not obstructed, and a down position in which a portion of the expanded section 930 adjacent to the valve is at least partially obstructed. The valve heads 927 may have the same stroke length (the distance traveled by the valve head between its up position and its down position), or the valve heads 927 may have different stroke lengths. The valves 925 may be positioned in any array adjacent to the expanded section 930 (i.e. in a straight line, or in a random array). Due to the large cross sectional area of the expanded region 930, when a valve head 927 is in its down position, flow of the fluid in the expanded region 930 is possible around the valve head.

Electric power from a power supply (not shown) is distributed among the valves 925 and 940 according to a predetermined temporo-spatial array by a driver unit (not shown).

When a valve head 942a or 942b is in its down position, the segment of the narrow region 935a or 935b, respectively, is obstructed. In use, a valve head 942a or 942b is brought to its down position so as to obstruct the narrow section 935a or 935b, respectively. One or more of the valve heads 927 are then brought to their down position so as to decrease to volume of the expanded section 930. The valve heads 927 may be brought to their down position, for example, either simultaneously or sequentially. When the valve head 942a is in its down position and the valve head 942b is in its up position, lowering one or more of the valve heads 927 will cause fluid to flow from the expanded section 930 in the narrow section 935b of the conduit 920. Similarly, when the valve head 942b is in its down position and the valve head 942a is in its up position, lowering one or more of the valve heads 927 will cause fluid to flow from the expanded section 930 in the narrow section 935a of the conduit 920. The pump 915 may thus be used to generate a flow from the expanded section 930 to either one of the narrow sections 935.

FIG. 10a shows a perspective view of a driving mechanism 120 that may be used in a pump of the invention. The mechanism 120 is shown in an exploded view in FIG. 10b, and a front view of the mechanism 120 is shown in FIGS. 11a to 11g. The mechanism 120 includes an X-shaped metal lever 122 pivotable around an axis 124. A first auxiliary lever 126 and a second auxiliary lever 128 also pivot around the axis 124. An electromagnet 130 is used to generate a magnetic field between a first metal core arm 132a and a second metal core arm 132b.

The lever 122 has four arms 134a, 134b, 134c, and 134d, with arms 134a and c diametrically opposite each other, and arms 134b and d diametrically opposite each other. The first auxiliary lever 126 has first and second arms 126a and b, and the second auxiliary lever 128 has first and second arms 128a and b.

Figure 11A:
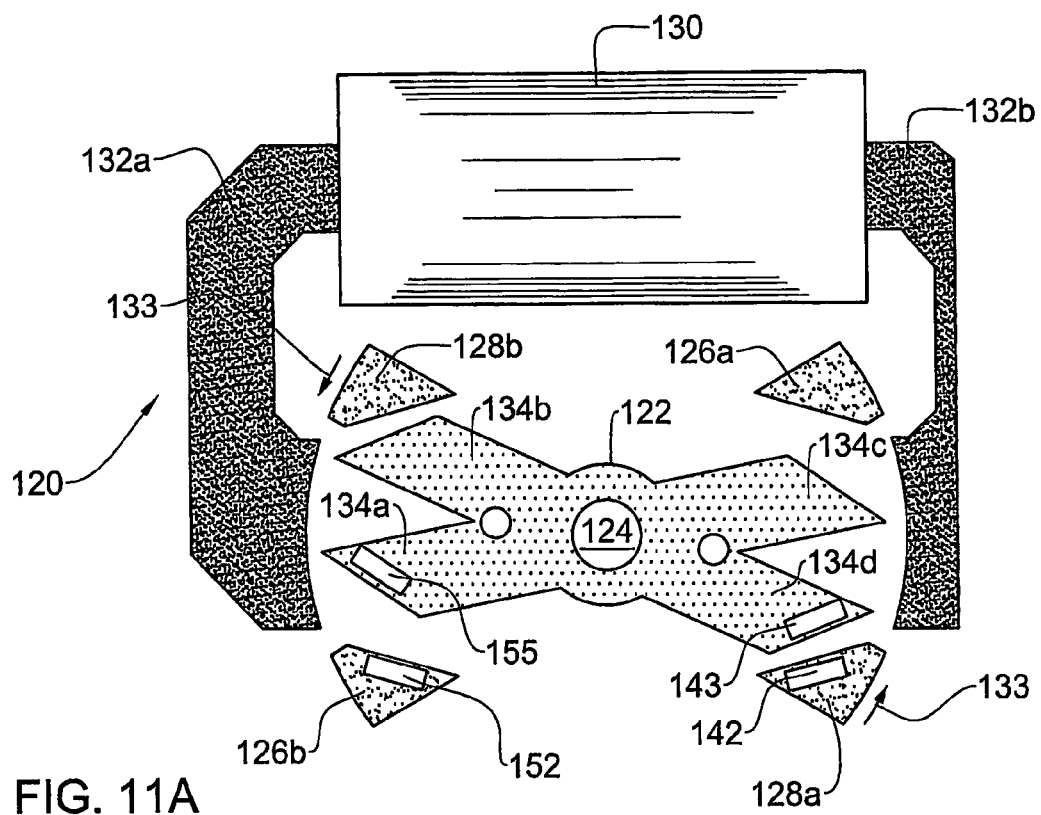
FIG. 11 shows stages in the mechanical cycle of the driving mechanism of FIG. 10.
Figure 11B:
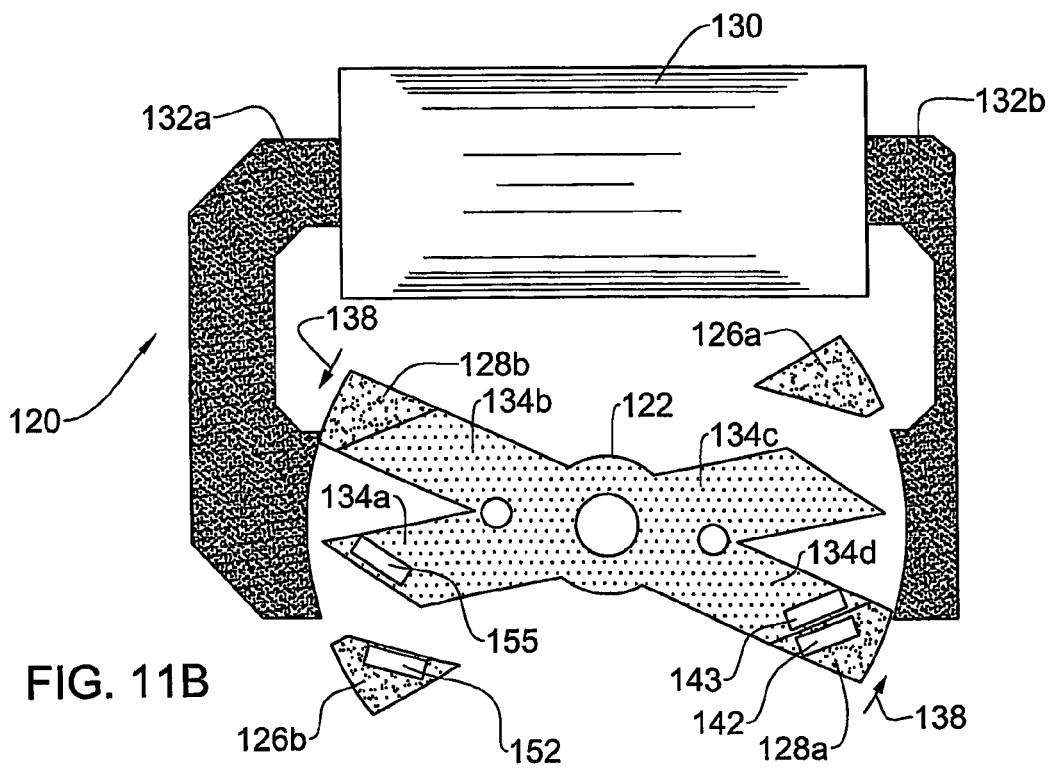
Figure 11C:
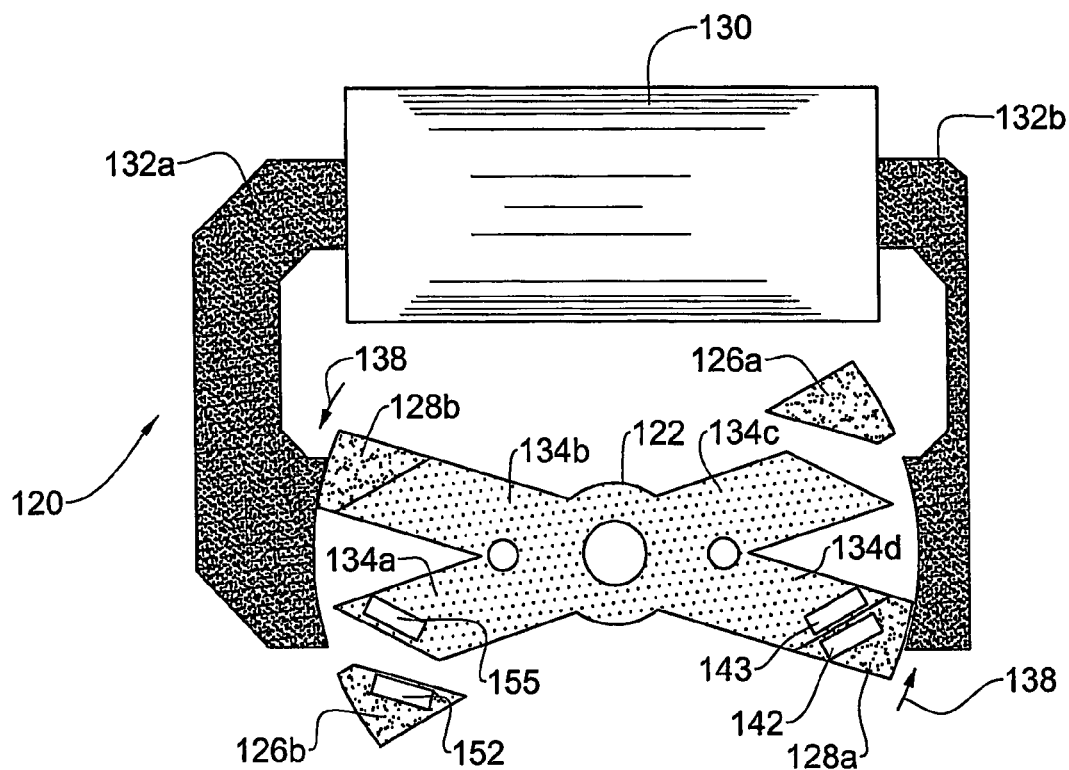
Figure 11D:
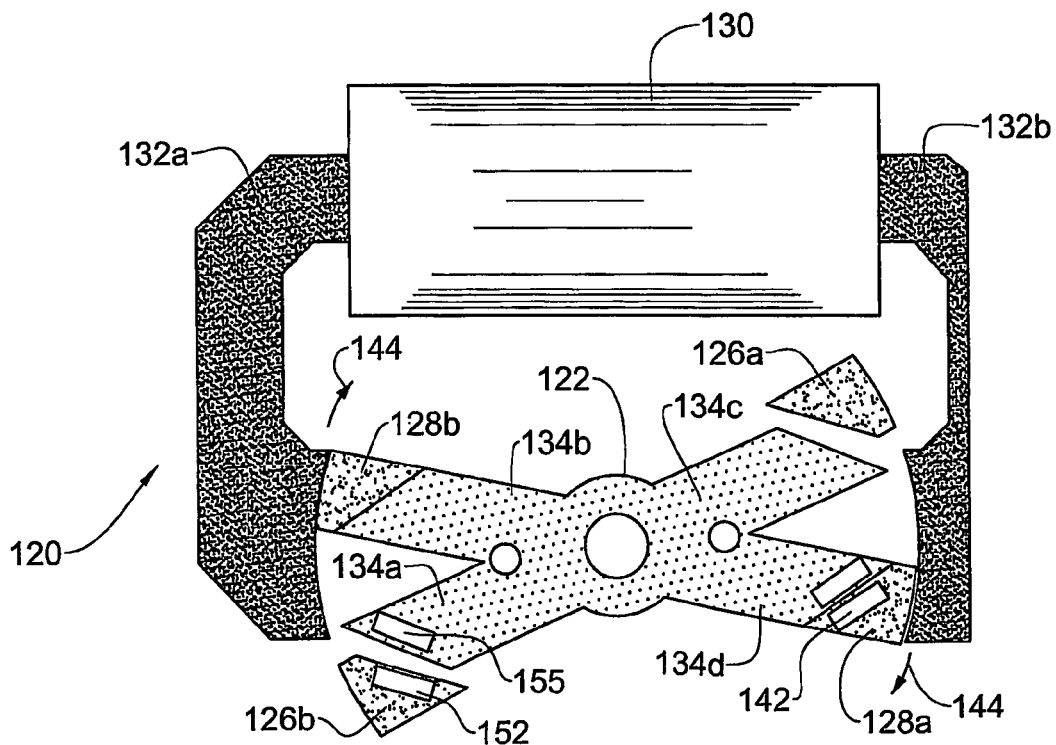

In FIG. 11a, the driving mechanism 120 is shown with the lever 122 in a configuration in which lever arms 134a and c are between the first and second core arms 132a and b, and lever arms 134b and d are outside the core arms 132a and b. The distance between the lever arm 134d and the first arm 128a and the distance between the lever arm 134b and the second arm 128b are both less than the distance between the lever arms 134c and a from the first and second arms 126a and b. When the electromagnet 130 is activated with the lever in the configuration shown in FIG. 11a, the second auxiliary lever 128 rotates counterclockwise in the direction of the arrows 133, until it contacts the lever arms 134b and d, as shown in FIG. 11b. The second auxiliary lever 128 continues to move counter clockwise in the direction of the arrows 133, urging the lever 122 counterclockwise in the direction of arrows 138 (FIGS. 11b and c). Counterclockwise movement of the lever 122 and the second auxiliary lever 128 continues until one of the valve heads contacts and obstructs the tubular conduit 905 (see FIG. 8). The mechanism 120 is now in the configuration shown in FIG. 11d.

The electromagnet 130 is then deactivated. A repulsion between the arm 128a and the arm 134d causes the second auxiliary lever 128 to rotate clockwise in the direction of the arrows 144 (FIG. 11d), until the mechanism 120 acquires the configuration shown in FIG. 11e. The repulsion may be due, for example to a first permanent magnet 142 located on the arm 128a and a second permanent magnet 143 located on the arm 134d, as shown in FIG. 11. Alternatively, the repulsion may be due to a spring mechanism (not shown).

Figure 11E:
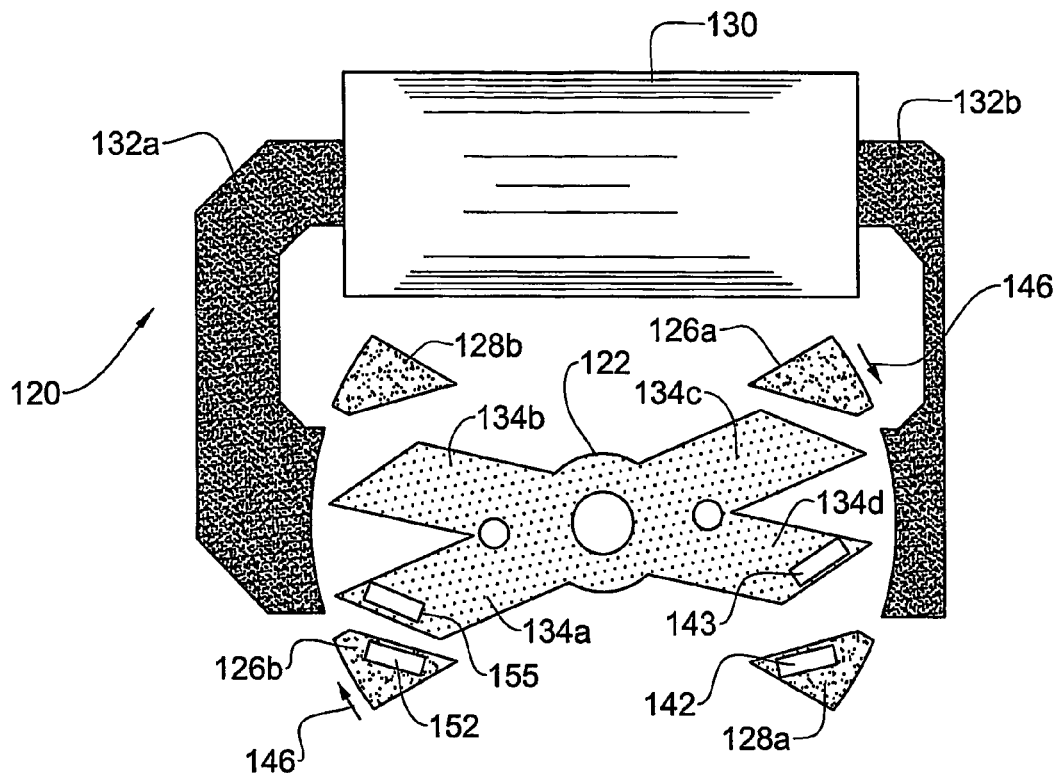
Figure 11F:
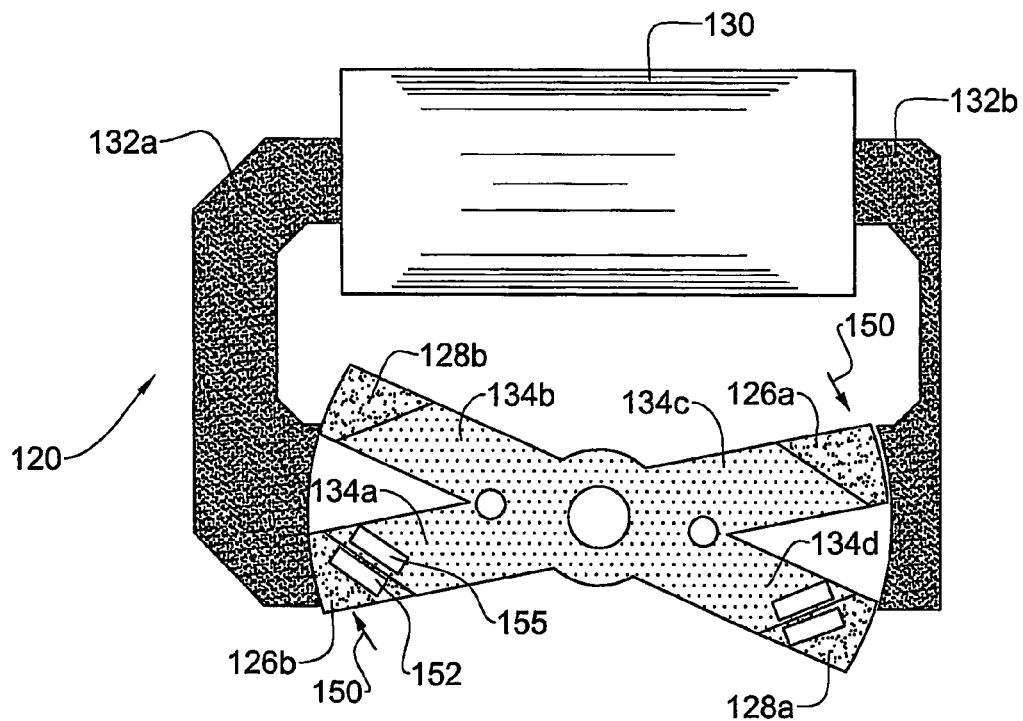
Figure 11G:
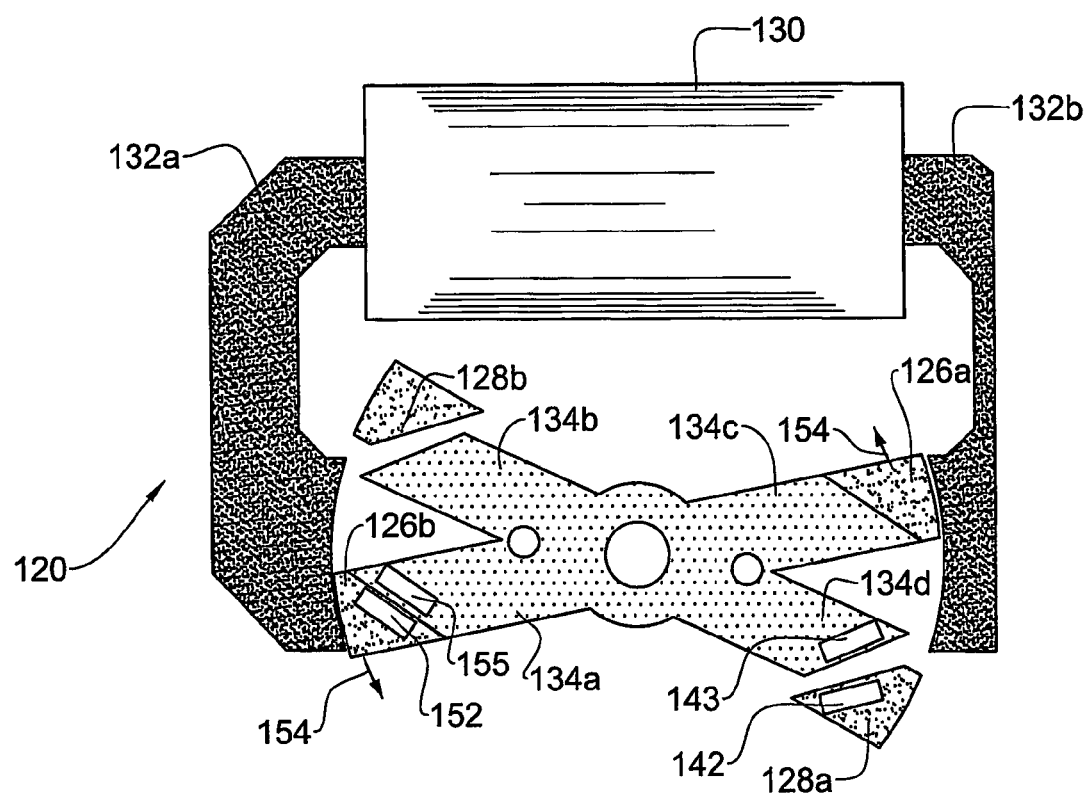

In the configuration shown in FIG. 11e, the lever arms 134b and d are between the first and second core arms 132a and b, and lever arms 134a and c are outside the core arms 132a and b. The distance between the lever arm 134d and the first arm 128a and the distance between the lever arm 134b and the second arm 128b are both greater than the distance between the lever arms 134c and a from the first and second arms 126a and b. The electromagnet 130 is now reactivated. The first auxiliary lever 126 rotates clockwise in the direction of the arrows 146, until it contacts the lever arms 134a and c, as shown in FIG. 11f. The first auxiliary lever 126 continues to move clockwise in the direction of the arrows 146, urging the lever 122 clockwise in the direction of arrows 150 (FIG. 11f). Clockwise movement of the lever 122 and the first auxiliary lever 126 continues until one of the valve heads contacts and obstructs the tubular conduit 905 (see FIG. 8).

The electromagnet 130 is then deactivated. A repulsion between the arm 126b and the arm 134a causes the first auxiliary lever 126 to rotate counterclockwise in the direction of the arrows 154 (FIG. 11g), until the mechanism 120 acquires the configuration shown in FIG. 11a. This repulsion may be due, for example, to a third permanent magnet 152 located on the arm 126b and a fourth permanent magnet 155 located on the arm 134a, or to a spring mechanism (not shown). The mechanical cycle of the mechanism 120 may then begin again.

Figure 12A:
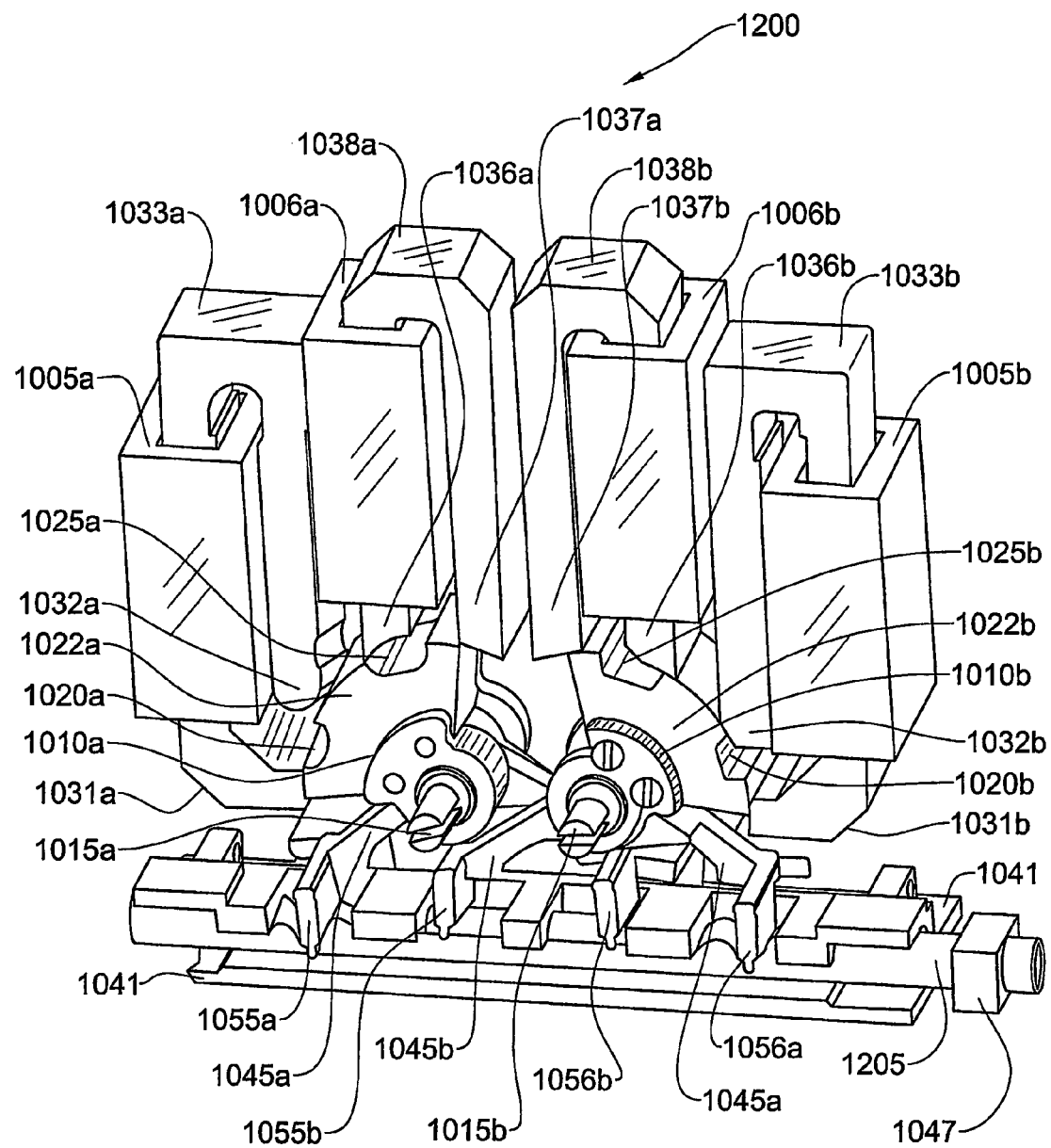
FIG. 12 shows a pump in accordance with another embodiment of the invention.
Figure 12B:
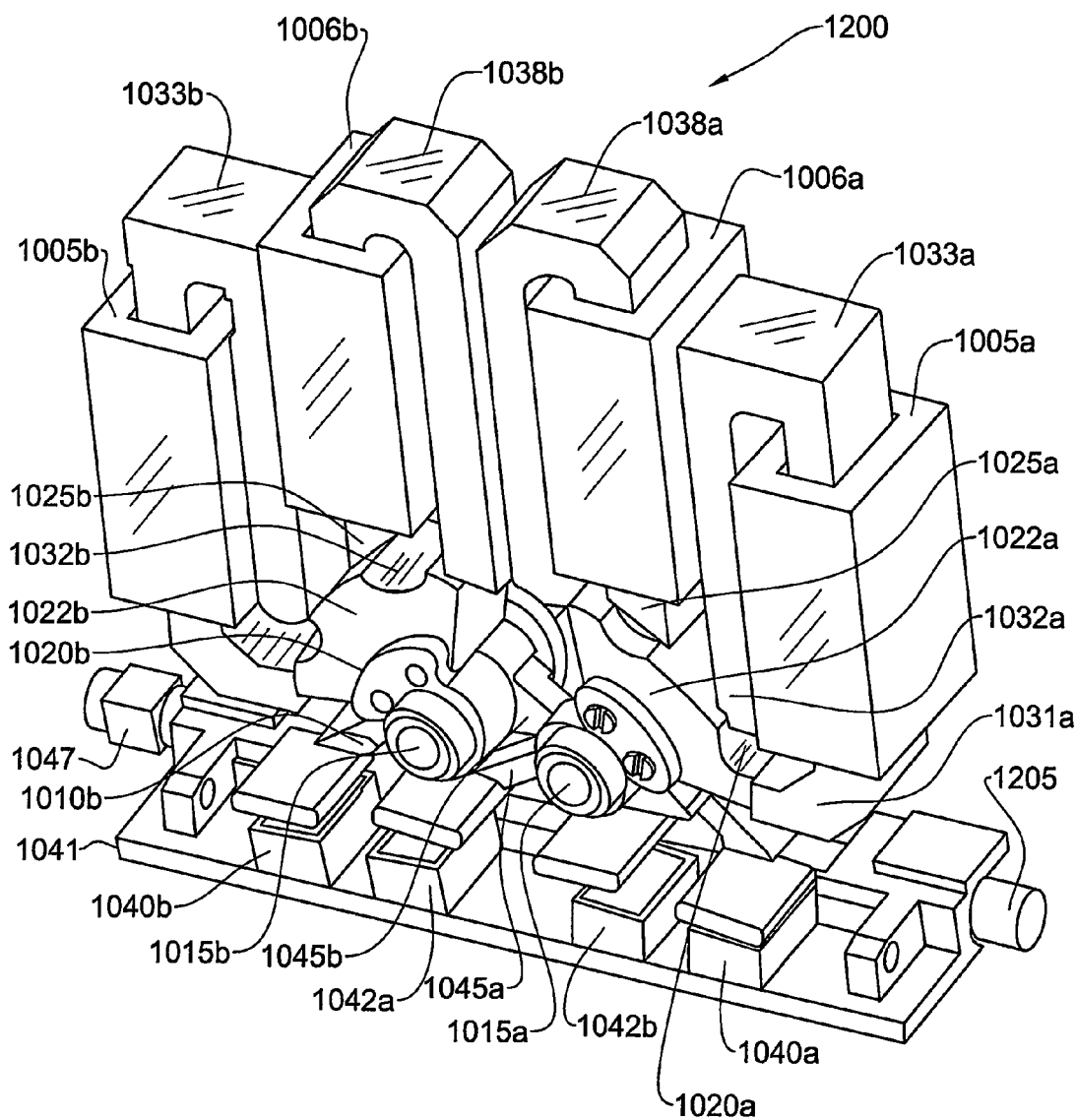

FIG. 12 shows a pump 1200 in accordance with another embodiment of the invention that executes the temporo-spatial array of valve activation shown in FIG. 4, to generate flow in an elastic tube 1205. The pump 1200 is shown in a front view in FIG. 12a, and in a rear view in FIG. 12b. In the pump 1200, a segmental actuator 1010a is rotatable around a pivot 1015a. The segmental actuator 1010a has a first notch 1020a and a second notch 1025a. The first notch 1020a and the second notch 1025a are separated by an inter-notch region 1022a. The position of the segmental actuator 1010a is determined by a pair of electromagnets 1005a and 1006a. When the electromagnet 1005a is activated, the segmental actuator 1010a rotates counter clockwise (when viewed from the perspective of FIG. 12a) so as to bring the first notch 1020a between a first end 1031a and a second end 1032a of a metal core 1033a. The segmental actuator thus assumes a first position shown in FIG. 12. When the electromagnet 1006a is activated, segmental actuator 1010a rotates clockwise (when viewed from the perspective of FIG. 12a) so as to assume a second position (not shown) in which the second notch 1025a is between a first end 1036a and a second end 1037a of a metal core 1038a.

A lever 1045a has a first valve head 1055a and a second valve head 1056a. The lever 1045a is fixed to the segmental actuator 1010a and rotates about the pivot 1015a from a first position in which the valve head 1055a is lower than the valve head 1056a, as shown in FIG. 12, and a second position in which the valve head 1055a is higher than the valve head 1056a (not shown). The lever 1045a is fixed to segmental actuator 1010a, so that the position of the lever 1045a is determined by the position of the segmental actuator 1010a. When the segmental actuator 1010a is in its first or second position, the lever 1045a is also in its first or second position, respectively. A permanent magnet 1040a, attached to the base 1041 of the pump, latches the lever 1045a and the segmental actuator 1010a in their first position. A permanent magnet 1042a, attached to the base 1041 of the pump, latches the lever 1045a and the segmental actuator 1010a in their second position.

A second segmental actuator 1010b is rotatable around a pivot 1015b. The segmental actuator 1010b has a first notch 1020b and a second notch 1025b. The first notch 1020b and the second notch 1025b are separated by an inter-notch region 1022b. The position of the segmental actuator 1010b is determined by a pair of electromagnets 1005b and 1006b. When the electromagnet 1005b is activated, the segmental actuator 1010b rotates clockwise (when viewed from the perspective of FIG. 12a) so as to bring the first notch 1020b between a first end 1031b and a second end 1032b of a metal core 1033b. The segmental actuator thus assumes a first position shown in FIG. 12. When the electromagnet 1006b is activated, segmental actuator 1010b rotates counterclockwise (when viewed from the perspective of FIG. 12a) so as to assume a second position (not shown) in which the second notch 1025b is between a first end 1036b and a second end 1037b of a metal core 1038b.

A lever 1045b has a first valve head 1055b and a second valve head 1056b. The lever 1045b is fixed to the segmental actuator 1010b and rotates about the pivot 1015b from a first position in which the valve head 1055b is lower than the valve head 1056b (not shown), and a second position in which the valve head 1055b is higher than the valve head 1056b, as shown in FIG. 12. The lever 1045b is fixed to 1010b, so that the position of the lever 1045b is determined by the position of the segmental actuator 1010b. When the segmental actuator 1010b is in its first or second position, the lever 1045b is also in its first or second position, respectively. A permanent magnet 1040b, attached to the base 1041 of the pump, latches the lever 1045b and the segmental actuator 1010b in their first position. A permanent magnet 1042b, attached to the base 1041 of the pump, latches the lever 1045b and the segmental actuator 1010b in their second position.

The temporo-spatial array of activation of the four electromagnets 1005a, 1006a, 1005b, and 1006b, is determined by a driver (not shown) so as to activate a predetermined temporo-spatial array of valve head positions. Valve heads 1055a, and 1056a are never open or closed simultaneously. The same also applies to 1055b and 1056b. This is consistent with the temporo-spatial array of valve head activation shown in FIG. 4.

Two or more pumps of the invention may be used simultaneously in a pumping system. For example, two pumps may be positioned in series along a conduit, or may be positioned in parallel along two branches or tributaries of a conduit.

The pump of the invention may further comprise an anti-free-flow device 1047 (see FIGS. 12a and 12b). The anti-free flow device prevents flow of liquid in the tube when the tube is being inserted or removed from the pump.

Figure 15:
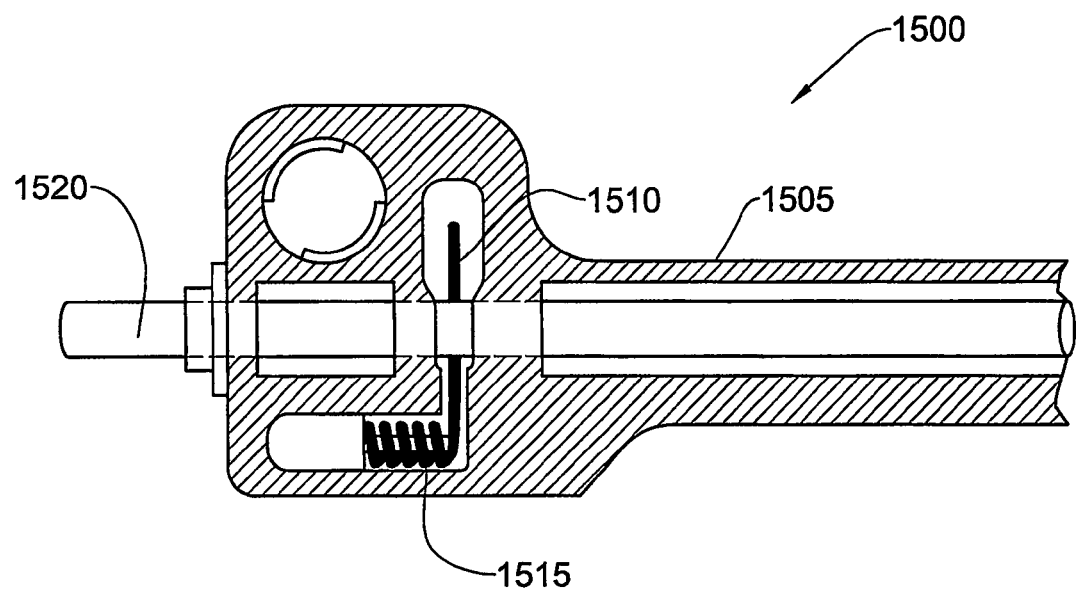
FIG. 15 shows an anti-free-flow device.

FIG. 15 shows an anti-free flow device 1500 that may be used with any of the pumps of the invention. The anti-free flow device 1500 includes a sleeve 1505 that contains a portion of a tube 1520. Lever 1510 is spring biased by a spring 1515 so as to press upon the tube 1520 so as to occlude the lumen of the tube 1520 when the device 1500 is not inside the pump. When the sleeve is in position inside the pump, and the pump door is closed, a pin located on the inside surface of the door depresses the lever 1510 away from its spring biased position so as to open the lumen of the tube 1520 and allow flow of liquid in the tube.

Figure 16:
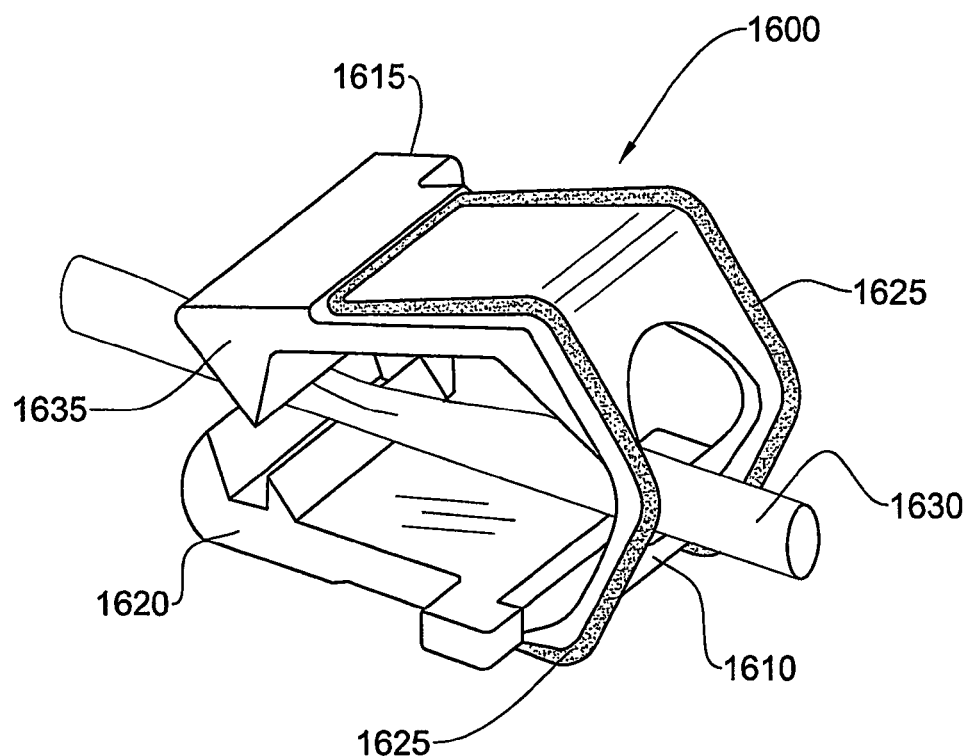
FIG. 16 shows another anti-free-flow device.

FIG. 16 shows another anti-free flow device 1600 that may be used with the pump of the invention. The anti-free flow device 1600 has a "C" shaped body 1610. The ends 1615 and 1620 are spring biased by a spring 1625 to press upon a tube 1630 so as to occlude the lumen of the tube 1630 when the device 1600 is not located inside the pump. When the device is inserted into the pump, the end 1615 of the body 1625 engages a member fixed in the pump having a slanted surface so as to urge it up from its spring biased position, so as to open the lumen of the tube 1630 and allow flow of liquid in the tube. The end 1615 has a slanted surface 1635.

Figure 13:
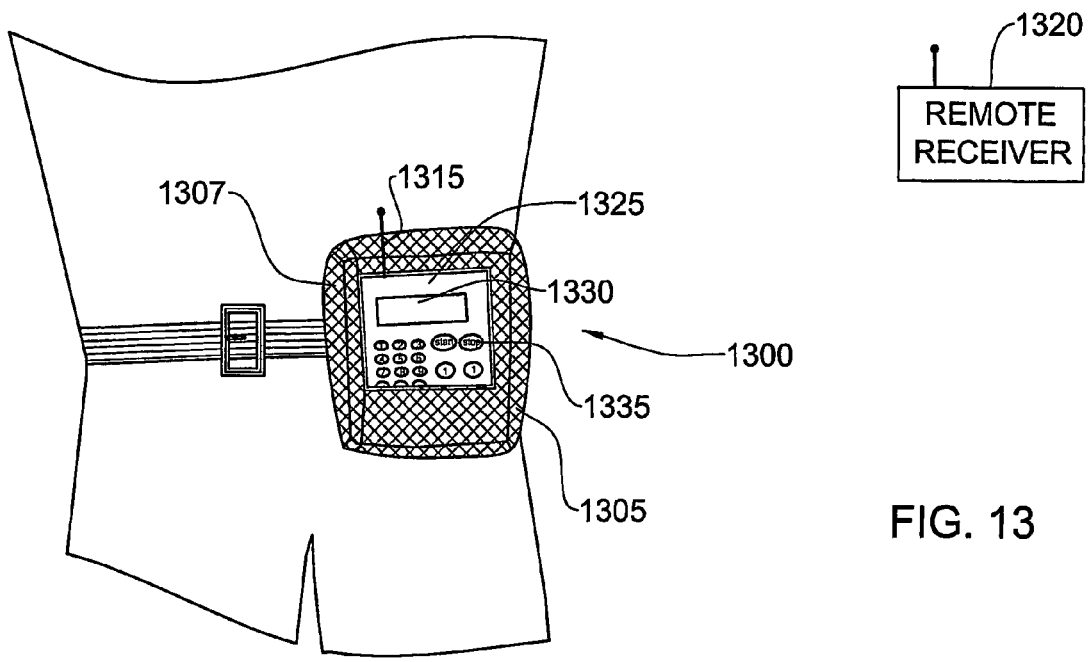
FIG. 13 shows a portable pump of the invention.
Figure 14:
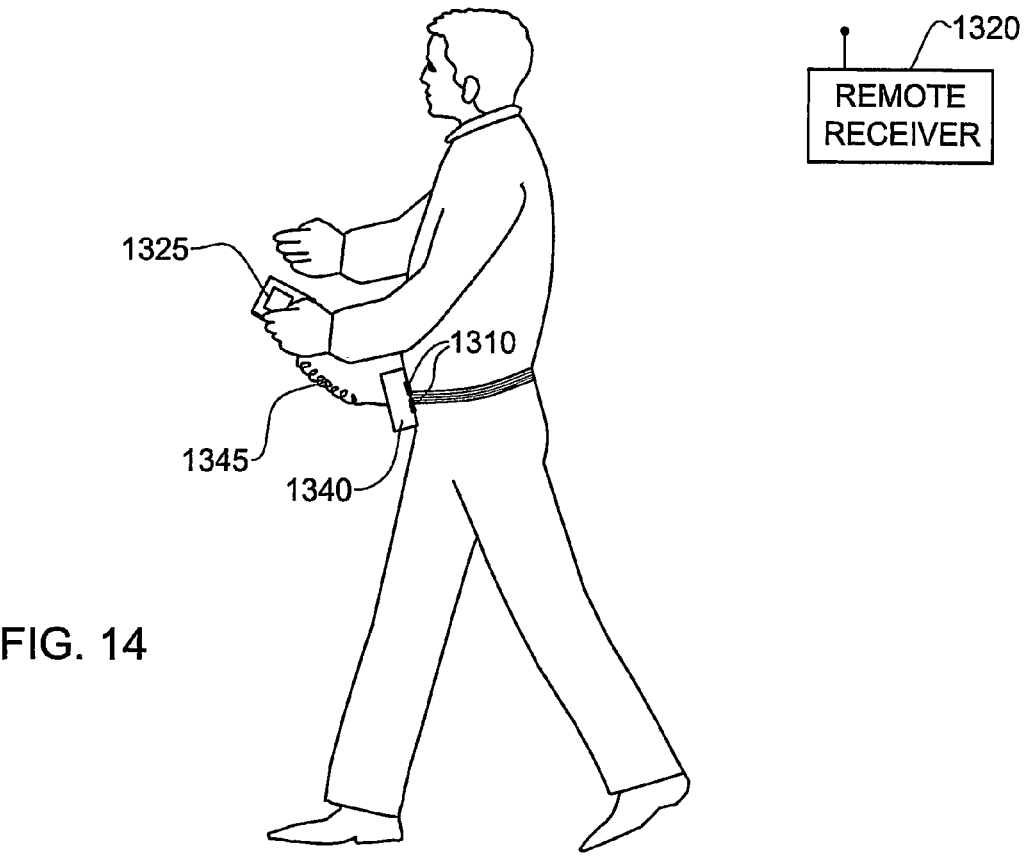
FIG. 14 shows the pump of FIG. 13 after detachment of the control panel.

In a preferred embodiment, the pump of the invention is powered by one or more batteries, so that the pump is portable as shown in FIGS. 13 and 14. As shown in FIG. 13, a portable pump 1300 of the invention 1300 may be received in a padded pouch 1305 that protects the pump 1300 from mechanical shocks during use. The pouch 1305 is provided with straps or clips 1310 in order to affix the pouch and pump onto a user's body or clothing. The pouch includes a container 1307 for a fluid that is to be pumped by the pump and infused into the user's body. The pump 1300 has a control panel 1325. The pump 1300 has a control panel 1325. The control panel 1325 has a display screen 1330 that displays various parameters of the pumps functioning (for example, the pumping rate, the total volume that has been pumped, the time that the pump has been in operation, or the occurrence of a malfunction in the pump) The control panel 1325 also has input buttons 1335 for selection of pump parameters, such as the pumping rate. The control panel 1325 may be detachable from the rest of the pump 1340, as shown in FIG. 14, in order to facilitate viewing of the display screen or input of pump parameters. The control panel 1325 may communicate with the rest of the pump 1340 by a cable 1345 that is retractable inside the pump and out of view when the control panel 1325 is attached to the rest of the pump 1340, as shown in FIG. 13. Alternatively, the control panel 1325 may communicate with the unit 1340 of the pump by a wireless connection (not shown). The pump 1300 may also be equipped with a transceiver 1315 communicating with a remote transceiver 1320. The transceiver 1315 may transmit to the remote transceiver 1320 information relating to operation of the pump such as the pumping rate, the total volume that has been pumped, the time that the pump has been in operation, or the occurrence of a malfunction in the pump. The remote transceiver 1320 may be used to program the pump in stead of the control panel 1325.

The invention claimed is:

1. A driving mechanism for use in a pump for generating fluid flow in an elastic tubular conduit having a lumen, the pump including:
    (a) four electrically operated valves, each valve being positionable adjacent to the conduit, each valve having a valve head, the valve head configured to alternate from a first position in which the lumen of the conduit adjacent to the valve head is unobstructed and a second position in which the lumen of the conduit adjacent to the valve head is obstructed; and
    (b) a driver, comprising at least one electromagnet, configured to control the positions of the valve heads, so as to execute a predetermined temporo-spatial array of valve head positions,
    the mechanism comprising:
    (a) an X shaped metal lever pivotable around an axis;
    (b) a first auxiliary lever pivotable about the axis;
    (c) a second auxiliary lever pivotable about the axis;
    (d) an intermittently activatable electromagnet generating, when activated, a magnetic field between a first metal core arm and a second metal core arm;
    wherein the magnetic field causes rotation of an auxiliary lever about the axis when extremities of the lever arm are not between the first and second core arms so as to bring the extremities between the first and second core arms.

2. A pump for generating fluid flow in an elastic tubular conduit having a lumen, comprising:
    (a) four electrically operated valves, each valve being positionable adjacent to the conduit, each valve having a valve head, the valve head configured to alternate from a first position in which the lumen of the conduit adjacent to the valve head is unobstructed and a second position in which the lumen of the conduit adjacent to the valve head is obstructed;
    (b) a driver, comprising at least one electromagnet, configured to control the positions of the valve heads, so as to execute a predetermined temporo-spatial array of valve head positions; and
    (c) a mechanism comprising:
    (a) an X shaped metal lever pivotable around an axis;
    (b) a first auxiliary lever pivotable about the axis;
    (c) a second auxiliary lever pivotable about the axis;
    (d) an intermittently activatable electromagnet generating, when activated, a magnetic field between a first metal core arm and a second metal core arm;
    wherein the magnetic field causes rotation of an auxiliary lever about the axis when extremities of the lever arm are not between the first and second core arms so as to bring the extremities between the first and second core arms.

* * * * *